United States Patent [19]

Adiletta

[11] Patent Number: 5,458,586
[45] Date of Patent: Oct. 17, 1995

[54] UNIVERSAL CONNECTOR FOR VACUUM SYSTEMS

[75] Inventor: Joseph G. Adiletta, Thompson, Conn.

[73] Assignee: Pall Corporation, East Hills, N.Y.

[21] Appl. No.: 339,739

[22] Filed: Nov. 14, 1994

[51] Int. Cl.$^6$ .................................................. A61M 25/00
[52] U.S. Cl. ........................ 604/283; 604/326; 604/905
[58] Field of Search .................................. 604/283, 264, 604/257, 280, 283, 326, 905, 206

[56] References Cited

U.S. PATENT DOCUMENTS

| | | | |
|---|---|---|---|
| 3,719,197 | 3/1973 | Pannier, Jr. et al. | 604/320 |
| 3,768,478 | 10/1973 | Fertik et al. . | |
| 3,982,538 | 9/1976 | Sharpe . | |
| 4,111,204 | 9/1978 | Hessel . | |
| 4,228,798 | 10/1980 | Deaton . | |
| 4,298,358 | 11/1981 | Ruschke . | |
| 4,396,016 | 8/1983 | Becker | 604/257 |
| 4,459,139 | 7/1984 | von Reis et al. | 604/320 |
| 4,561,868 | 12/1985 | von Reis et al. . | |
| 4,714,464 | 12/1987 | Newton | 604/118 |
| 4,738,668 | 4/1988 | Bellotti et al. | 604/29 |
| 4,740,202 | 4/1988 | Stacey et al. . | |
| 4,886,498 | 12/1989 | Newton | 604/118 |
| 4,935,010 | 6/1990 | Cox et al. | 604/122 |
| 5,015,369 | 5/1991 | Romine et al. | 604/27 |
| 5,071,403 | 12/1991 | Larsson . | |
| 5,100,376 | 3/1992 | Blake, III . | |
| 5,137,031 | 8/1992 | Guirguis | 128/762 |
| 5,183,472 | 2/1993 | Jaehrling et al. | 604/905 |
| 5,185,007 | 2/1993 | Middaugh et al. . | |
| 5,238,655 | 8/1993 | Laible et al. | 128/766 |
| 5,351,674 | 10/1994 | Hawks | 604/41 |

OTHER PUBLICATIONS

Eval. of Air Assay Media by the Monodisperse DOP Smoke Test, ASTM, Designation: D 2986–71 (Reapproved 1978), pp. 132–138.
Vac-Rite promotional material, 2 pages (no date).
Water Resistance of Coated Cloth:High Range, Hydrostatic Pressure Federal Test Method Standard No. 191, Method 5512, Dec. 31, 1968.
Water Resistance of Coated Cloth:Low Range, Hydrostatic Pressure Federal Test Method Standard No. 191, Method 5514, Dec. 31, 1968.

Primary Examiner—C. Fred Rosenbaum
Assistant Examiner—N. Kent Gring
Attorney, Agent, or Firm—Leydig, Voit & Mayer

[57] ABSTRACT

Universal connectors suitable for use during the operation of vacuum or aspiration systems are disclosed.

13 Claims, 3 Drawing Sheets

UNIVERSAL CONNECTOR FOR VACUUM SYSTEMS

TECHNICAL FIELD

This invention relates to universal connectors for use in vacuum systems, e.g., systems providing for aspiration or drainage of fluids. Preferably, the present invention provides a universal connector for use in vacuum systems involving laser surgery.

BACKGROUND OF THE INVENTION

During the utilization of some systems providing for vacuum or suction, it may be desirable to move a fluid from one location to another. For example, during surgery, a suction receptacle may be connected to a vacuum source to draw various body fluids, e.g., blood, from the site of the operation through a tube for deposit and collection in a fluid collection receptacle. Typically, suction systems utilize a fluid collection receptacle and a cover which are secured together in fluid tight fashion to form a fluid collection device. Two connections are provided in the cover, one to be connected by a tube to the source of the vacuum, for example, a vacuum pump or hospital vacuum outlet station. The other connection is connected through a drainage tube to provide fluid communication with the particular area of the patient requiring drainage. The vacuum pressure applied to the receptacle carries fluid through the drainage tube to a fluid inlet port in the receptacle cover.

Since the elements of the vacuum system, e.g., the vacuum pump, and/or the vacuum regulator, may be damaged or contaminated by undesirable material such as the body fluid, the microorganisms such as bacteria associated with the body fluid and/or the debris associated with the surgery, the fluid collection device and/or the vacuum system may include a specialized structure such as a filter or a valve that prevents the passage of the body fluid (or aerosol particles thereof), microorganisms, and/or debris to the source of the vacuum.

Some fluid aspiration protocols may include a specialized filter in the vacuum system. For example, one system utilizes a filter device including a hydrophobic filter and a hydrophilic filter. The hydrophilic filter is positioned just upstream of and preferably in contact with the inlet surface of the hydrophobic filter. As the hydrophilic filter becomes totally saturated with liquid, it blocks or substantially restricts the passage of air therethrough to the hydrophilic filter, thereby signalling the need to replace the device. However, this device suffers from drawbacks in that the hydrophilic filter may be slow to fill, since, for example, the rate of water absorption of the hydrophilic filter may vary with the flow rate of the fluid, and with the wicking property of the hydrophilic filter. This may make the process rather unpredictable, and may lead to an undesirably large pressure differential.

In some systems, the inside surface of the receptacle cover may include a filter mounted thereto, e.g., upstream of the line leading to the vacuum source, so that the filter fits within the receptacle when the cover is sealed to the receptacle. In addition to requiring a specialized filter, this system requires particular fluid collection receptacles and matching covers, which must be designed to allow sufficient room for the filter. Such specialized devices may be more expensive and/or more difficult to manufacture than conventional collection receptacles and covers.

There are additional drawbacks to this type of system. Since different filters may be optimal for different applications, e.g., involving other body fluids and/or other medical procedures, a hospital may prefer to carry a wide variety of these specialized receptacle devices, to ensure that the optimum filter is available for a particular application. This entails additional expense and effort resulting from purchasing and maintaining the inventory of these different devices.

Accordingly, there is an unaddressed need in the art for a universal connector that provides fluid communication between components of a vacuum system, and prevents contamination of the vacuum system by predictably and efficiently preventing the flow of undesirable material such as laser-created smoke, body fluid, aerosols, microorganisms, and/or debris through the connector.

There is also an unmet need for a universal connector that would be compatible with a variety of fluid collection receptacles and aspiration protocols. Even more advantageously, such a connector should be compatible with a variety of existing vacuum or suction systems, without modification of the existing system(s). For example, the universal connector should be compatible with conventional central vacuum systems having suction powers generally operating up to about 30 inches Hg. Among other advantages, such a universal connector would allow a hospital to reduce its inventory of different collection receptacles while providing suitable filtration for a wide variety of protocols.

SUMMARY OF THE INVENTION

In accordance with the present invention, a universal connector for use in suction and/or vacuum systems comprises a housing including an inlet and an outlet and defining a fluid flow path between the inlet and the outlet, and, located between the inlet and the outlet, a barrier arrangement providing for varied hydrophobicity and preventing the passage of undesirable material such as laser created smoke, liquid, debris, and/or microorganisms therethrough.

Connectors produced in accordance with the invention have universal application, and are compatible with a variety of fluid collection devices and systems. Preferably, universal connectors according to the invention may be inserted in conventional and/or commercially available vacuum systems without modification to the existing system. In some embodiments, a plurality of connectors may be utilized to provide for, for example, increased dirt capacity and/or a desirable pressure differential.

The present invention provides at least one connector for use in any suction, vacuum, and/or aspiration system wherein it is desirable to prevent the passage of undesirable material such as laser-created smoke, liquid, debris and/or microorganisms. The present invention is particularly suitable for any vacuum and/or suction system in which body fluids may be collected, e.g., in a medical procedure such as surgery, more preferably, surgery involving cauterization, and/or laser surgery. The present invention may also be utilized during a postoperative protocol.

Embodiments of the present invention ameliorate at least some of the disadvantages of the prior art aspiration system protocols. These and other advantages of the present invention will be apparent from the description as set forth below.

SPECIFIC DESCRIPTION OF THE INVENTION

In accordance with the present invention, a connector for use in aspiration systems comprises a housing including an inlet and an outlet and defining a fluid flow path between the inlet and the outlet, and, located between the inlet and the outlet and across the fluid flow path, a barrier arrangement providing for varied hydrophobicity and preventing the passage of undesirable material such as liquid, debris, and/or microorganisms therethrough. In a preferred embodiment, the connector precludes the passage of laser-created "smoke" and associated debris, e.g., protein particles, as well as precluding the passage of microorganisms, more particularly, bacteria, therethrough.

Preferably, the connector comprises a housing wherein the inlet and outlet are adapted or configured for ease of connection to components of a vacuum system. For example, the inlet and outlet may comprise a universal fitting or coupler such as a luer fitting; a push-on fitting such as a barb type fitting; and the like. In a preferred embodiment, the connector also includes, between the inlet and the outlet, a barrier arrangement including at least two, and even more preferably, at least three, layers or zones of different hydrophobicity, wherein the liquid, debris and/or microorganisms are prevented from passing through the connector. In one preferred embodiment, at least one layer or zone comprises a prefilter such as a depth filter.

In one embodiment of the invention, a connector for use in an aspiration system comprises a housing including an inlet and an outlet, wherein the inlet and the outlet comprise barbed, push-on fittings, and, interposed between the inlet and the outlet, a laminated assembly comprising two or more layers of different hydrophobicity. In some embodiments, as will be noted in more detail below, the invention encompasses a plurality of connectors, e.g., two or more universal connectors capable of being arranged in parallel.

According to an embodiment of the invention, a method is provided comprising creating a negative pressure differential sufficient to allow gas or air flow through at least one universal connector, and to allow a fluid such as a body fluid to flow into a receiving container; and, preventing the passage of undesirable material from the receiving container through universal connector. In a preferred embodiment, the passage of body fluid through the connector is prevented. In an even more preferred embodiment of a method in accordance of the invention, the connector automatically prevents the passage of laser smoke and bacteria therethrough.

In some embodiments, a negative pressure differential is created sufficient to allow to allow gas or air flow through a plurality of universal connectors, e.g., arranged in parallel, and to allow a fluid such as a body fluid to flow into a receiving container; and, passage of undesirable material from the receiving container through the universal connectors is prevented.

Figure 1:
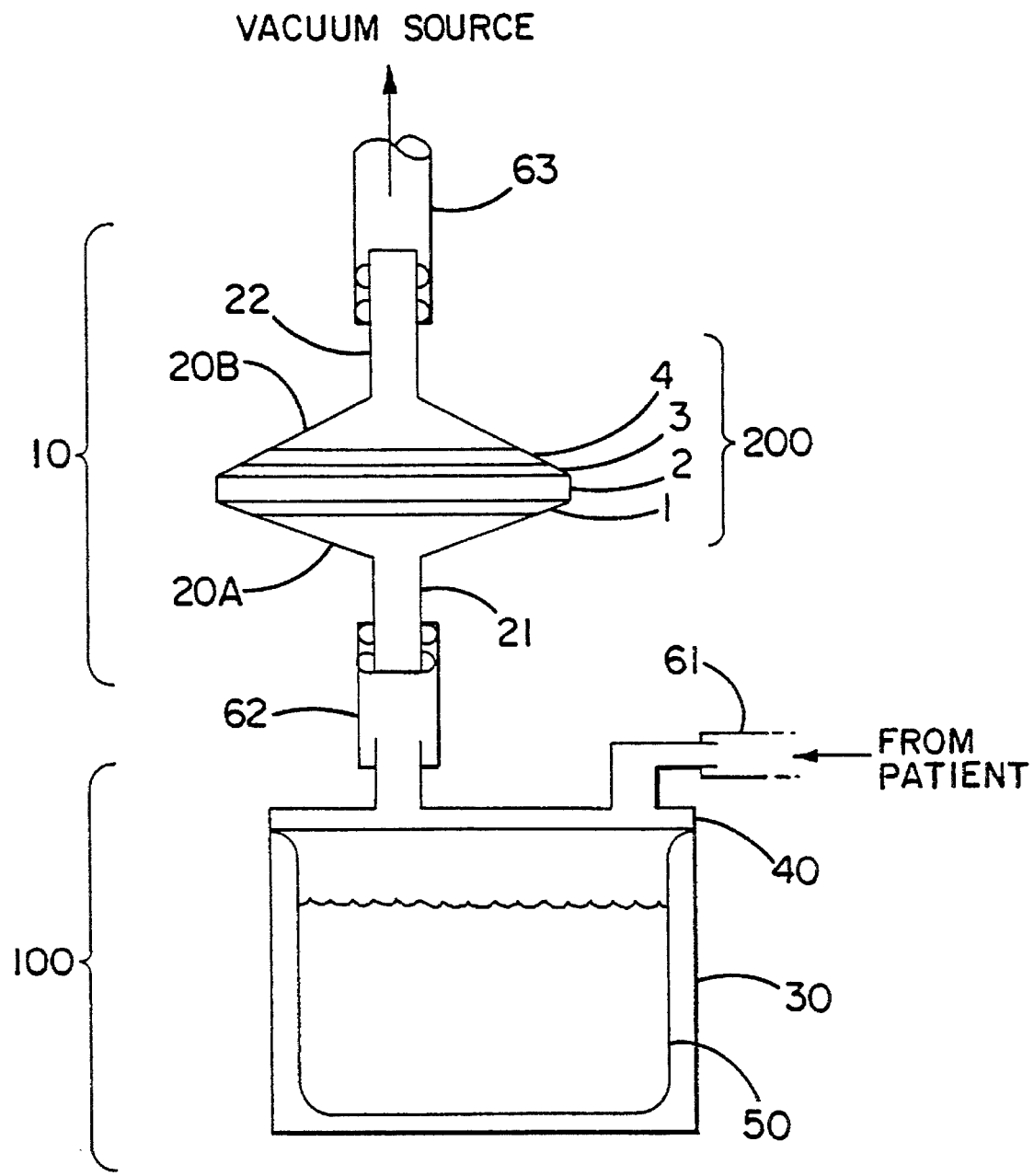
FIG. 1 is an embodiment of the present invention.
Figure 2:
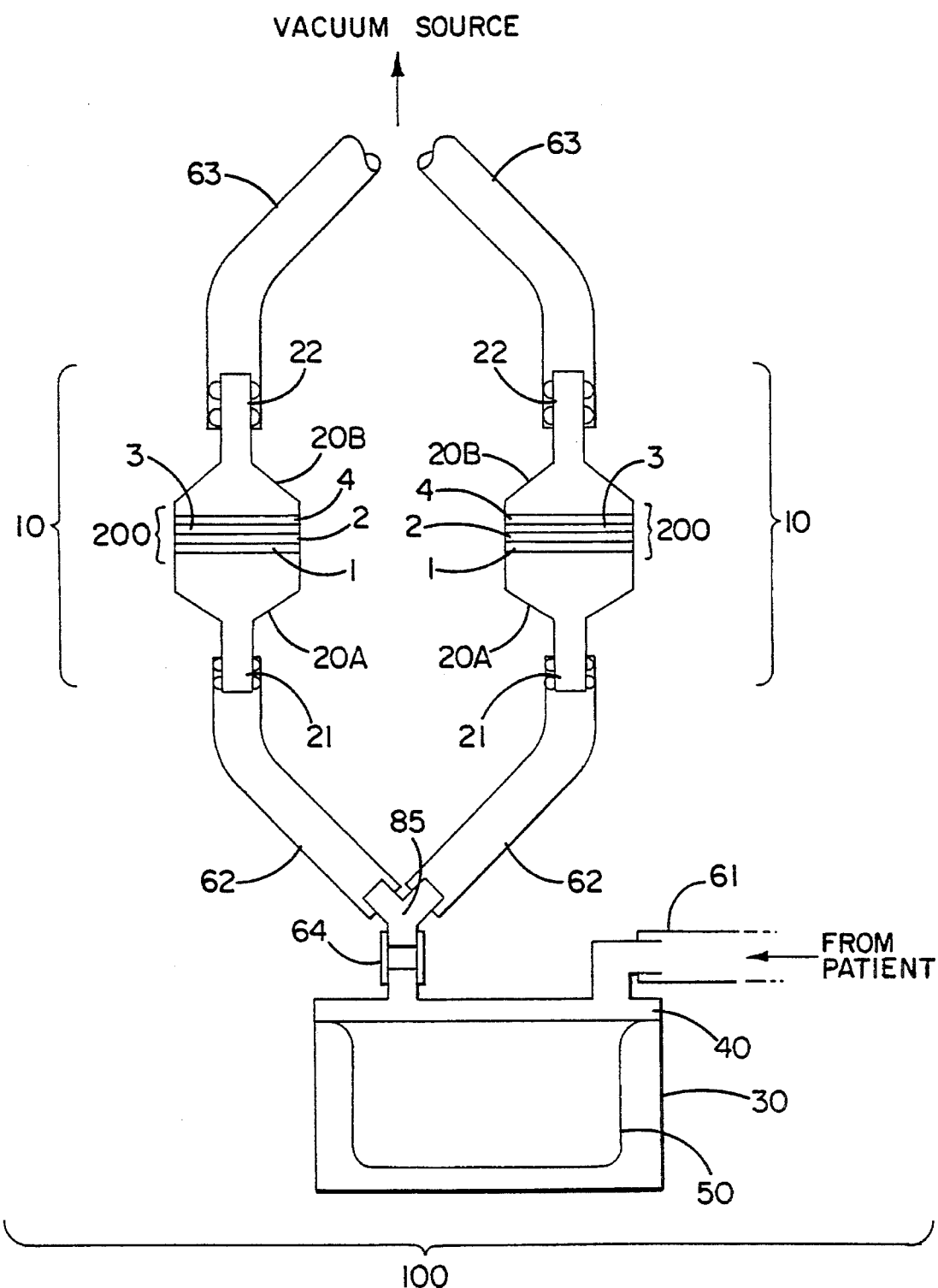
FIG. 2 is an embodiment of the present invention illustrating a plurality of universal connectors in series.

In accordance with an embodiment of the invention, as illustrated in FIGS. 1 and 2, a connector 10 for use in vacuum systems comprises a housing including a first portion 20A, and a second portion 20B, as well as an inlet 21 and an outlet 22 defining a fluid flow path through the connector. A barrier arrangement 200 providing for varied hydrophobicity is interposed between the inlet and the outlet across the fluid flow path.

In a preferred embodiment of the invention, the inlet 21 and/or the outlet 22 are adapted or configured for ease of providing fluid communication with the other components of the vacuum system. For example, in a more preferred embodiment of the invention, wherein the vacuum system includes conduits 62, 63, such as flexible plastic tubing, the inlet 21 and the outlet 22 of the connector 10 comprise fittings suitable for slidable, e.g., push-on, coupling to or connection with, the plastic tubing. Illustratively, the inlet and outlet fittings include barbs for more secure push-on coupling to the tubing. In other embodiments, the inlet and/or outlet may include, for example, luer fittings.

The housing may be fabricated from any suitably rigid, impervious material, including any impervious thermoplastic material, which is compatible with the body fluid being processed. For example, the housing may be fabricated from a metal, such as stainless steel, or from a polymer. In an embodiment, the housing is fabricated by injection molding from a polymer, more preferably a transparent or translucent polymer, such as an acrylic, or a polycarbonated resin. In some embodiments, the housing may be fabricated from a transparent or translucent polymer such as polypropylene, polystyrene, or polyethylene. Not only are such housings easily and economically fabricated, but also they allow observation of the passage of the liquid into the housing. The housing may include an arrangement of one or more channels, grooves, conduits, passages, ribs or the like which may be serpentine, parallel or curved, or a variety of other configurations to provide for more efficient flow of fluid and/or gas.

The surfaces of the housing contacting the fluid may be treated or untreated. Methods for treating the surface of the housing include but are not limited to radiation grafting and gas plasma treatment.

Any housing of suitable shape to provide an inlet, an outlet, and an adequate flow area may be employed.

The barrier arrangement 200 may be arranged in the housing as is known in the art. For example, the arrangement may be sealed within the housing via insert molding; thermal-press sealing; welding, e.g., ultrasonic or heat welding; edge crimping; interference fit; and the like. Similarly, the first portion 20A and a second portion 20B of the housing may be sealed in any suitable manner as is known in the art.

A barrier arrangement 200, in accordance with the invention, comprises a porous structure providing for a varied or graded hydrophobicity that is capable of precluding the passage of undesirable material therethrough. Accordingly, barrier arrangement 200 comprises two or more sections or regions of different hydrophobicity. Preferably, barrier arrangement 200 comprises at least two layers or zones, each having a different hydrophobicity.

Generally, hydrophobicity refers to a lack of affinity with water. A hydrophobic material has a critical wetting surface tension (CWST) lower than the surface tension of the liquid (i.e., water, having a surface tension of 73 dynes/cm) contacting the material, and is not readily or spontaneously wetted by the contacting liquid. Hydrophobic materials may be characterized by a high contact angle between a drop of water placed on the surface, and the surface. Such a high contact angle indicates poor wetting. Accordingly, a barrier arrangement in accordance with the invention is not wetted by, or poorly wetted by, water.

Since the arrangement has a varied hydrophobicity, at least one section or region of the arrangement may have a CWST closer to (but less than) the surface tension of a water, i.e., 73 dynes/cm, while another section or region of the arrangement may have a greater hydrophobicity, i.e., a lower CWST. One description of CWST can be found in, for example, U.S. Pat. No. 4,925,572, which is incorporated by references in its entirety.

Alternatively, or additionally, the hydrophobicity may be described with respect to water penetration. For example, hydrophobicity may refer to water pressure penetration measured using the test system as shown in FIG. 3.

Illustratively, the material to be tested may be sealed in a holding fixture including an open face clamp. Water is gravity fed at a steady rate by the flow meter/control valve, and the sample surface is observed through the open face clamp until a water entry bead appears. The pressure on the upstream side of the test sample is then determined by reading the mark on the transparent water column manometer. Of course, other testing techniques for determining water pressure penetration, including those summarized in Federal Test Method Standard No. 191, method 5512 (31 Dec. 1968), which includes the use of a piston to apply water pressure to the underside of the clamped specimen, and a pressure gauge to measure the pressure; and method 5514 (31 Dec. 1968), which are incorporated by reference in their entireties, may also be suitable.

In one embodiment, at least one of the more hydrophobic layers or zones in accordance with the invention comprises a membrane having a liquid rated pore size in the range of about 0.2 to about 0.4 microns. Alternatively, or additionally, at least one of the more hydrophobic layers or zones in accordance with the invention comprises a membrane having an aerosol rated pore size less than about 0.3 microns. Under typical flow conditions, a preferred membrane in accordance with the invention provides for retaining airborne bacteria particles in the range from about 0.2 to about 0.5 microns.

Figure 3:
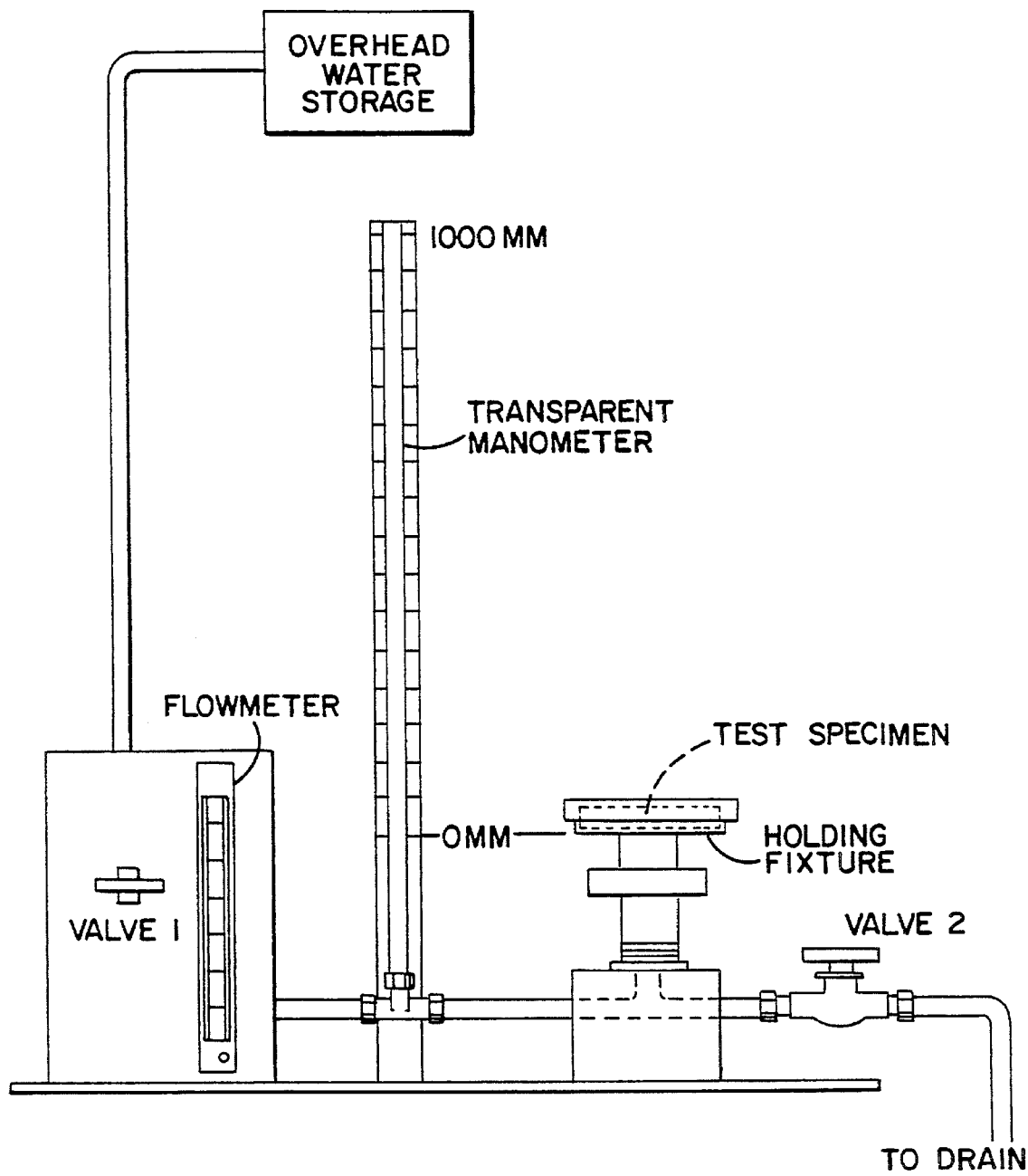
FIG. 3 is an elevation view of an apparatus to measure water repellency of materials such as the hydrophobic materials used in accordance with the invention.

Typically, when tested using the test system of FIG. 3, the membrane has a hydrophobic resistance of at least about 20 to about 40 p.s.i., or more, when the water column is at a height that correlates to a suction power of about 10 to about 20 p.s.i. Preferably, at least one membrane has a hydrophobic resistance of at least about 25 to about 35 p.s.i., when the water column is at a height that correlates to a suction power of about 12 to about 15 p.s.i. Of course, the membrane can have the hydrophobic resistance referenced above, i.e., at least about 20 to about 40 p.s.i., or more; more preferably, at least about 25 to about 35 p.s.i., when tested using Federal Test Method Standard No. 191, method 5512 (31 Dec. 1968) and method 5514 (31 Dec. 1968). Suitable membranes include, for example, membranes commercially available from Pall Corporation (East Hills, N.Y.) as Emflon-II™.

Other layers or zones may be less hydrophobic, e.g., have a hydrophobic resistance of less than about 40 p.s.i. where the suction power is as described above. Media suitable for these additional layers or zones include, for example, media commercially available from Pall Corporation (East Hills, N.Y.) as Tissuglass™.

In an embodiment, at least one layer or zone has a pore size of less than about 1 micron liquid rated, e.g., in the range of about 0.05 to about 1.0 microns. More preferably, at least one layer or zone has an pore size in the range of about 0.2 to about 0.4 microns liquid rated, e.g., about 0.3 microns liquid rated. With respect to the aerosol pore size, e.g., as tested by the DOP (dioctyl phthalate) smoke test (ASTM designation D2986-71 (Reapproved 1978), which is incorporated by reference in its entirety, at least one layer or zone preferably has an aerosol pore size of less than about 0.3 micron, more preferably, less than about 0.1 micron.

Typically, the layer(s) with the lower hydrophobicity will be more upstream than the layer(s) with the higher hydrophobicity. For example, with respect to the embodiment illustrated in FIG. 1, the most upstream layer 1 (i.e., the first layer to be contacted by the fluid), has a relatively low hydrophobicity; and a more downstream layer 3 has a greater hydrophobicity.

In a preferred embodiment, the barrier arrangement 200 includes at least three layers, each having a different hydrophobicity. Accordingly, with respect to FIG. 1, barrier arrangement 200 may include an additional layer 2, e.g., interposed between layers 1 and 3, having a different hydrophobicity than either of these layers. Preferably, layer 2 has a hydrophobicity between that of layer 1 and layer 3, i.e., more hydrophobic than layer 1, and less hydrophobic than layer 3.

In a preferred embodiment, comprising at least two zones or layers of different hydrophobicity, the barrier arrangement 200 may include at least one additional layer or zone to provide, for example, at least one of additional filtering (e.g., prefiltering), protecting the arrangement, support, binding, and sealing. With respect to binding and sealing, at least one layer or zone may provide for binding or sealing the layers of the arrangement (e.g., to form a laminate), and/or binding or sealing the arrangement to a housing.

In one embodiment, involving a medical procedure such as laser surgery or cauterization surgery, the barrier arrangement prevents the passage therethrough of the laser-created or cauterizing "smoke" and associated debris, e.g., at least one of solid debris such as bone and/or tissue particles; liquid debris including blood and "protein" particles, created during laser surgery and/or cauterization. For example, a preferred barrier arrangement includes at least one zone or layer, e.g., arranged at a more upstream section of the arrangement, comprising a prefilter, e.g., a depth filter, to efficiently filter the debris such as fine "protein" particles that could coat a membrane with an almost impermeable fine layer of particles and thus reduce air flow. In a preferred embodiment, the most upstream layer or zone of the barrier arrangement 200, e.g., layer 1, comprises a prefilter having a high dirt capacity.

In some embodiments, the barrier arrangement may include at least two prefilter layers or zones, e.g., at least two depth filter layers or zones. Preferably, the barrier arrangement includes two prefilter layers and/or zones that provide for high dirt capacity and long life by minimizing the amount of particles (e.g., sticky protein particles) reaching a liquid and/or microorganism blocking layer or zone. For example, with respect to an embodiment of the illustrated barrier arrangement 200, wherein layer 3 bars the passage therethrough of laser smoke, body fluid, and bacteria under typical aspiration and/or vacuum system conditions (e.g., wherein the suction power is less than about 20 p.s.i.), prefilter layers 1 and 2 minimize the amount of particles reaching layer 3.

In a preferred embodiment, including at least two prefilter layers, e.g., layers 1 and 2, the layers provide a graded pore structure and/or a graded depth. For example, upstream prefilter layer 1 may include larger pores and/or less densely packed fibers than prefilter layer 2. Prefilter layer 1 may comprise a higher loft, higher dirt capacity layer having larger average diameter fibers than prefilter layer 2. Suitable media providing for prefiltration and varied hydrophobicity include, for example, commercially available media from Pall Corporation (East Hills, N.Y.) as AQU-BLK™.

As noted above, the barrier arrangement may include at least one layer for at least one of protection, binding and sealing. For example, with respect to FIG. 1, barrier arrangement 200 may include layer 4 to protect at least one layer of the arrangement (e.g., layer 3) and/or to better seal the arrangement to the housing. Illustratively, layer 4 may protect layer 3 during manufacture, e.g., covering layer 3 during lamination to prevent layer 3 from being nicked or cut.

The barrier arrangement may include at least one non-hygroscopic zone or layer, e.g., interposed between layers of different hydrophobicity. In one embodiment, a non-hygroscopic zone or layer may be used to provide a bond between these other layers. In accordance with the invention, the term "hydrophobic" is to be distinguished from "non-hygroscopic." Hydrophobicity refers to water repellency, while the term non-hygroscopic refers to non-absorbency of water. A non-hygroscopic fiber will not absorb water. Illustratively, a metal layer or medium is more hygroscopic than a cotton layer or medium, even though both media may be hydrophobic.

The characteristics and/or composition of a layer or zone may vary in accordance with, for example, the type and/or composition of the body fluid flowing from the receiving container, the type of microorganism to be blocked, and the medical protocol being conducted.

Illustratively, individual layers or zones may differ from each other with respect to at least one of composition, and configuration. For example, with respect to composition, at least one layer or zone, e.g., providing prefiltration, may comprise at least one of glass and/or latex; and another layer or zone, e.g., providing a bacterial and liquid barrier, may comprise at least one of polytetrafluoroethylene (PTFE); polyvinylidene fluoride (PVDF) and ultra-high molecular weight polyethylene (UHMWPE). As noted earlier, one example of a commercially available product that is suitable for laser surgery, and provides a plurality of layers of varied hydrophobicity is AQU-BLK™ from Pall Corporation (East Hills, N.Y.). In one preferred embodiment, the barrier arrangement comprises a laminate including a plurality of layers.

With respect to configuration, at least one zone or layer may be arranged to form at least one of a membrane, a depth filter, a mat, and net. At least one layer may comprise a planar or corrugated sheet.

The present invention is compatible with a variety of aspiration and vacuum systems, including conventionally available systems. In an exemplary embodiment, a system in accordance with the invention includes at least one connector and two or more conduits in fluid communication with the connector. The system may include additional components such as but not limited to at least one flow control device, e.g., at least one clamp, valve, and the like; and a fluid collection receptacle.

In the embodiment illustrated in FIG. 1, system 100 includes a connector 10, as described above, in fluid communication, via a conduit 62 such as a flexible tube, with a fluid collection receptacle 30. The fluid collection receptacle 30 may include a receptacle cover 40, and the system may include a collection container 50, such as a disposable collection bag, more preferably a flexible bag, arranged within the collection receptacle 30. In the illustrated embodiment, system 100 includes conduits 61 and 63, which provide fluid communication with, respectively, the source of the liquid, e.g., the body fluid, and the source of the suction or vacuum. In another embodiment of the system, as illustrated in FIG. 2, two connectors 10 are arranged in parallel, with one end of each of conduits 62 in fluid communication with each of inlets 21, and the other end of each of conduits 62 in fluid communication with receptacle 30, via a fitting 85 and a conduit 64.

In carrying out a method in accordance with the present invention, the connector 10 may be used in a variety of aspiration and vacuum protocols, including conventional protocols, as is known in the art. For example, with respect to the embodiments illustrated in FIGS. 1 and 2, the connector 10 is placed in fluid communication with a source of vacuum, and a body fluid receiving container, e.g., a fluid collection receptacle 30 and a receptacle cover 40, via conduits 62 and 63. Since the inlet 21 of first housing portion 20A and the outlet 22 of second housing portion 20B are adapted to provide fluid communication with the other components of the aspiration system, conduits 62 and 63 are easily and securely coupled, preferably, slidably mounted, to the inlet 21 and the outlet 22, respectively. In a more preferred embodiment, slidably coupling the conduits to the connector includes engaging the inner surface of the conduit 62 with the exterior surface of the inlet 21, and engaging the inner surface of the conduit 63 with the exterior surface of the outlet 22.

A hospital aspiration or vacuum system may be operated to draw air or gas through connector 10 by passing the air or gas through inlet 21, barrier arrangement 200, and outlet 22, and to draw a patient's body fluid and debris from the drainage site, through a conduit 61, into a fluid collection receptacle 30. In accordance with a method provided by the invention, undesirable material(s), particularly body fluid and laser smoke, are prevented from passing through the connector 10. In an even more preferred embodiment, microorganisms are also prevented from passing through the connector.

Under typical conditions, e.g., using a suction system providing a suction power of less than about 20 p.s.i., e.g., less than about 15 p.s.i., the connector will prevent the passage of liquid therethrough when the collection container is full. Of course, in some embodiments, the connector will prevent the passage of liquid therethrough using suction systems providing much higher suction power.

In a preferred embodiment, the connector automatically prevents the passage of liquid therethrough. However, in some embodiments, a flow control device, e.g., interposed between the inlet of the connector and the outlet of the fluid collection receptacle, may be manually operated to prevent flow through the filter assembly.

In some embodiments, a plurality of connectors may be utilized. For example, as illustrated in FIG. 2, two or more connectors 10 may be arranged in parallel. The use of connectors is parallel may be advantageous for those embodiments wherein a low differential pressure and/or extra debris capacity may be desirable. Illustratively, the use of a plurality of connectors provides extra surface area for blocking the passage of undesirable material such as body fluid and/or debris, since each connector includes a barrier arrangement. Since the surface area is increased, and less undesirable material is passed to any one connector, extra undesirable material, which could increase the pressure differential between the inlet and the outlet of a single connector if the material contacted one barrier arrangement, is blocked, while minimizing the pressure differential.

Similar to the configuration illustrated in FIG. 1 (like reference numbers are used for like components), since the inlets 21 and the outlets 22 in FIG. 2 are adapted to provide fluid communication with the other components of the aspiration system, conduits 62 and 63 are easily and securely coupled to the inlets and the outlets 22, respectively. The hospital suction system may be operated as described previously.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

I claim:

1. A connector for use in an aspiration system comprising:
   a plastic housing including an inlet and an outlet and defining a fluid flow path through the housing;
   said inlet including a first fitting adapted to provide fluid communication with the aspiration system;
   said outlet including a second fitting adapted to provide fluid communication with the aspiration system;
   said connector including a barrier assembly arranged within the housing between the inlet and the outlet and across the fluid flow path, said assembly including at least two hydrophobic layers of different hydrophobicity;
   said connector being capable of preventing the passage of undesirable material therethrough.

2. The connector of claim 1 wherein the first fitting comprises a push-on fitting including barbs slidably sealable with the inner surface of a first flexible tube of an aspiration system, and the second fitting comprises a push-on fitting including barbs slidably sealable with the inner surface of a second flexible tube of the aspiration system.

3. The connector of claim 1 wherein the barrier assembly comprises a laminate.

4. The connector of claim 1 wherein said connector is suitable for use in an aspiration system during laser surgery.

5. The connector of claim 4 wherein said connector is capable of preventing the passage of protein particles therethrough.

6. The connector of claim 1 wherein said connector is capable of preventing the passage of protein particles therethrough.

7. The connector of claim 1 wherein said connector is capable of preventing the passage of body fluid therethrough.

8. The connector of claim 1 wherein said connector is capable of preventing the passage of body fluid and protein particles therethrough.

9. The connector of claim 1 including at least three hydrophobic layers of different hydrophobicity.

10. The connector of claim 9 wherein at least one layer comprises a depth filter.

11. A method for operating an aspiration system during surgery comprising:
    coupling a first conduit of an aspiration system and a second conduit of an aspiration system to a connector, said first and second conduits each having a first end and a second end, and an inner surface;
    said connector comprising:
      a plastic housing including an inlet adapted to provide fluid communication with the first conduit and an outlet adapted to provide fluid communication with the second conduit, and defining a fluid flow path between the inlet and the outlet, and including a barrier arrangement between the inlet and the outlet across the fluid flow path, said arrangement providing for at least two hydrophobic layers of different hydrophobicity;
    wherein coupling the first conduit to the connector comprises slidably engaging the inner surface of the first end of the first conduit with an exterior surface of the inlet of the connector; and,
    wherein coupling the second conduit to the connector comprises slidably engaging the inner surface of the first end of the second conduit with an exterior surface of the outlet of the connector;
    placing the second end of the second conduit in fluid communication with an aspirator;
    placing the first end of the first conduit in fluid communication with a body fluid receiving container;
    activating the aspirator to create a negative pressure differential sufficient to allow air to flow through the connector via the inlet, the barrier arrangement and the outlet, wherein the negative pressure differential allows body fluid to flow into the receiving container; and,
    preventing the passage of body fluid from the receiving container through the connector.

12. The method of claim 11 including passing body fluid and protein particles into the receiving container, and preventing the passage of the body fluid and the protein particles from the receiving container through the connector.

13. The method of claim 11 including preventing the passage of body fluid and laser created smoke from the receiving container through the connector.

* * * * *